United States Patent [19]

Mackenzie et al.

[11] Patent Number: 5,300,516
[45] Date of Patent: Apr. 5, 1994

[54] MUSCARINIC RECEPTOR ANTAGONISTS

[75] Inventors: Alexander R. Mackenzie, Deal; Peter E. Cross, Canterbury, both of England

[73] Assignee: Pfizer Inc., New York, N.Y.

[21] Appl. No.: 859,728

[22] PCT Filed: Nov. 28, 1990

[86] PCT No.: PCT/EP90/02040
§ 371 Date: Jun. 11, 1992
§ 102(e) Date: Jun. 11, 1992

[87] PCT Pub. No.: WO91/09014
PCT Pub. Date: Jun. 27, 1991

[30] Foreign Application Priority Data

Dec. 12, 1989 [GB] United Kingdom ............... 8928043

[51] Int. Cl.$^5$ .............. A61K 31/445; C07D 211/88; C07D 401/04; C07D 405/14
[52] U.S. Cl. .................. 514/320; 514/252; 514/318; 514/319; 514/321; 514/326; 514/328; 544/336; 546/193; 546/195; 546/197; 546/205; 546/212; 546/219
[58] Field of Search ............. 544/336; 546/193, 205, 546/195, 197, 212, 219; 514/252, 318, 319, 320, 321, 328, 326

[56] References Cited

U.S. PATENT DOCUMENTS

| | | | |
|---|---|---|---|
| 2,664,424 | 12/1953 | Hoffman | 546/219 |
| 2,848,455 | 8/1958 | Hoffman | 546/219 |
| 3,125,578 | 3/1964 | Jassen | 546/187 |
| 3,963,729 | 6/1976 | Gittos | 546/188 |

FOREIGN PATENT DOCUMENTS 2206491 1/1989 United Kingdom ............... 546/219

Primary Examiner—C. Warren Ivy
Assistant Examiner—Celia Chang
Attorney, Agent, or Firm—Peter C. Richardson; Paul H. Ginsburg

[57] ABSTRACT

Musacarinic receptor antagonists, particularly useful in the treatment of irritable bowel syndrome, of formula (I), or a pharmaceutically acceptable salt thereof, where m is 1 or 2; $R^1$ and $R^2$ are each independently H or $C_1$-$C_4$ alkyl or together represent —$(CH_2)_p$— where p is an integer of from 2 to 5; $R^3$ is H or $C_1$-$C_4$ alkyl; wherein Z is a direct link; —$CH_2$—, —$CH_2O$— or —$CH_2S$—; and $R^4$ is a group of formulae (II), (III), (IV) or Het, where $R^5$ and $R^6$ are each independently H, $C_1$-$C_4$ alkyl, $C_1$-$C_4$ alkoxy, —$(CH_2)_n$OH, halo, trifluoromethyl, cyano, —$(CH_2)_n$NR$^7$R$^8$, —CO($C_1$-$C_4$ alkyl), —OCO($C_1$-$C_4$ alkyl), —CH(OH)($C_1$-$C_4$ alkyl), —C(OH)($C_1$-$C_4$ alkyl)$_2$, —$SO_2NH_2$, $(CH_2)_n$CONR$^7$R$^8$ or —$(CH_2)_n$COO($C_1$-$C_4$ alkyl); $R^7$ and $R^8$ are each independently H or $C_1$-$C_4$ alkyl; n is 0, 1 or 2; X and $X^1$ are each independently O or $CH_2$; q is 1, 2 or 3; and "Het" is pyridyl, pyrazinyl or thienyl.

8 Claims, No Drawings

MUSCARINIC RECEPTOR ANTAGONISTS

BACKGROUND OF THE INVENTION

This invention relates to certain 3-phenylglutarimide derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oescophageal achalasia and chronic obstructive airways disease.

SUMMARY OF THE INVENTION

According to the invention, there are provided compounds of the formula:

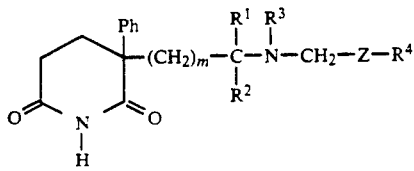

and their pharmaceutically acceptable salts, where m is 1 or 2;

$R^1$ and $R^2$ are each independently H or $C_1$–$C_4$ alkyl or together represent —$(CH_2)_p$— where p is an integer of from 2 to 5;

$R^3$ is H or $C_1$–$C_4$ alkyl;

wherein

Z is a direct link; —$CH_2$—, —$CH_2O$— or —$CH_2S$—; and $R^4$ is a group of formula:

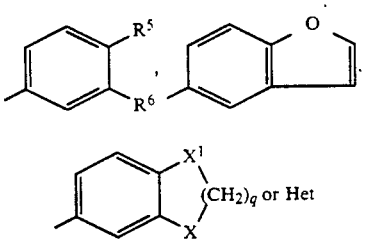

where $R^5$ and $R^6$ are each independently H, $C_1$–$C_4$ alkyl, $C_1$–$C_4$ alkoxy, —$(CH_2)_nOH$, halo, trifluoromethyl, cyano, —$(CH_2)_nNR^7R^8$, —$CO(C_1$–$C_4$ alkyl), —O-$CO(C_1$–$C_4$ alkyl), —$CH(OH)(C_1$–$C_4$ alkyl), —C-$(OH)(C_1$–$C_4$ alkyl)$_2$, —$SO_2NH_2$, —$(CH_2)_nCONR^7R^8$ or —$(CH_2)_nCOO(C_1$–$C_4$ alkyl);

$R^7$ and $R^8$ are each independently H or $C_1$–$C_4$ alkyl;

n is 0, 1 or 2;

X and $X^1$ are each independently O or $CH_2$;

q is 1, 2 or 3; and

"Het" is pyridyl, pyrazinyl or thienyl.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

m is preferably 2.

$R^1$ and $R^2$ are preferably each H or $CH_3$.

$R^3$ is preferably methyl, Z is preferably —$CH_2$—.

$R^4$ is preferably a group of the formula:

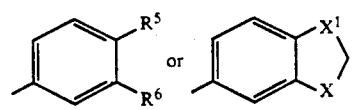

where $R^5$ and $R^6$ are each independently selected from H, halo, hydroxy, and $C_1$–$C_4$ alkyl, and X and $X^1$ are as defined above.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol, and recovering the acid addition salt either as a precipitate, or by evaporation of the solution.

DETAILED DESCRIPTION OF THE INVENTION

The compounds of the formula (I) can be prepared by the following route:

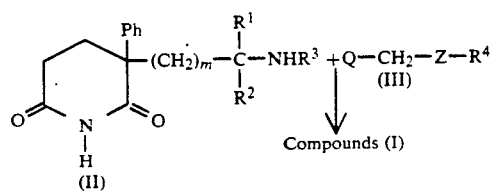

$R^1$, $R^2$, $R^3$, $R^4$, Z and m are as defined for formula (I) and Q is a leaving group, e.g. Br, Cl, I, $C_1$–$C_4$ alkanesulfonyloxy (e.g. methanesulfonloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate, sodium bicarbonate, triethylamine or pyridine, and in a suitable organic solvent, e.g. acetonitrile, at up to the reflux temperature. Reaction temperatures of 60°–120° C. are generally desirable and it is most convenient to carry out the reaction under reflux.

In the preferred technique, the compounds (II) and (III) are refluxed together in acetonitrile in the presence of sodium bicarbonate. The product (I) can be isolated and purified conventionally.

The starting materials of the formula (II) can be obtained by conventional procedures such as those described in the following Preparations section. The starting materials of the formula (III) are in general known compounds which can be prepared by conventional techniques. The preparation of any novel starting materials of the formula (III) used in the Examples is however described in the following Preparations section.

A typical route to the compounds (II) is as follows:

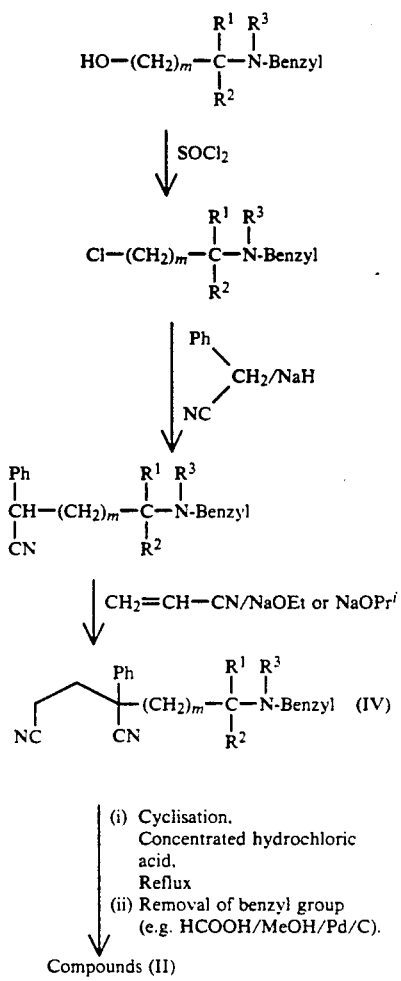

(i) Cyclisation.
Concentrated hydrochloric acid.
Reflux
(ii) Removal of benzyl group
(e.g. HCOOH/MeOH/Pd/C).

Compounds (II)

The compounds of the formula (I) can also be prepared by the cyclisation of the compounds of the formula (V):

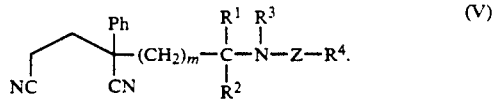

The cyclisation is typically carried out using concentrated mineral acid, preferably concentrated hydrochloric acid, typically under reflux.

The starting materials (V) can be prepared analogously to the previously-described method for preparing the N-benzyl intermediates (IV).

Some of the compounds of the formula (I) in which $R^4$ is a substituted phenyl group can be converted to other compounds of the formula (I) as follows:

(a) A —$CO_2(C_1-C_4$ alkyl) substituent on the phenyl group can be selectively reduced to —$CH_2OH$. Lithium aluminum hydride is the most suitable reducing agent. The reaction is typically carried in a suitable organic solvent, e.g. ether, at between 0° and room temperature. It is generally most convenient to use the starting material in the form of its methyl ester.

(b) A hydroxy substituent on the phenyl group can be converted to —$OCO(C_1-C_4$ alkyl) by acylation using a $C_1-C_4$ alkanoyl chloride or bromide, or an alkanoic anhydride of the formula $(C_1-C_4$ alkyl.CO$)_2$O. The presence of an acid acceptor is preferable. The reaction is typically carried out at about room temperature in a suitable organic solvent, e.g. dioxan.

(c) A —$CO(C_1-C_4$ alkyl) substituent on the phenyl group can be reduced to a substituent of the formula —$CH(OH)(C_1-C_4$ alkyl). A suitable reducing agent is sodium borohydride. The reaction is typically carried out at between 0° and room temperature in a suitable organic solvent, e.g. methanol.

(d) A —$(CH_2)_nCOO(C_1-C_4$ alkyl) substituent, preferably where the alkyl group is methyl, can be converted to —$(CH_2)_nCONR^7R^8$ by reaction with ammonia or the appropriate amine $R^7R^8NH$. When $R^7$ and $R^8$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may proceed at a satisfactory rate at room temperature, heating at up to 120°, preferably 60° to 100° C., is generally necessary. For volatile amines, the reaction is best carried out in a bomb.

(e) A hydroxymethyl or hydroxyethyl substituent on the phenyl group can be converted to —$CH_2NR^7R^8$ or —$(CH_2)_2NR^7R^8$ firstly by reaction with thionyl chloride and secondly be reaction with ammonia or the appropriate amine $R^7R^8NH$. The reaction with thionyl chloride is typically carried out with heating, preferably under reflux, in a solvent such as methylene chloride. The reaction with ammonia or the amine is typically carried out at in a solvent such as ethanol, and heating, e.g. under reflux, may be necessary.

(f) A —$CO(C_1-C_4$ alkyl) substituent can be converted to —$C(OH)(C_1-C_4$ alkyl$)_2$ by reaction with a $C_1-C_4$ alkyllithium or $C_1-C_4$ alkylmagnesium bromide, chloride, or iodide (e.g. methyllithium, methylmagnesium bromide, methylmagnesium iodide or methylmagnesium chloride). The reaction is typically carried out in a solvent such as ether at a temperature of from 0° C. to room temperature. and (g) An iodo substituent can be converted to $C_1-C_4$ alkoxycarbonyl by reaction, typically at about room temperature, with carbon monoxide in a $C_1-C_4$ alkanol containing a base [e.g. potassium carbonate] and a palladium (II) catalyst [e.g. bis(triphenylphosphine)palladium (II) chloride].

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylchpoline (ileum) or carbachol (trachea, bladder and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of the test compound and the above procedure is repeated. Typically four concentrations of the test compound are evaluated on each tissue.

The concentration of the test compound which causes a doubling of the agonist concentration to produce the original response is determined ($pA_2$ value —Arunlakshana and Schild (1959), Brit. J. Pharmacol., 14, 48–58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curvative or prophylactic treatment of diseases associated with the altered motility and/or tone of smooth muscle, such as irritable bowel syndrome, diverticular disease, urinary incontinence oescophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there will, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or of a pharmaceutically acceptable salt thereof, for the manufacture of a medicament for the treatment of diseases associated with the altered motility and/or tone of smooth muscle, such as irritable bowel syndrome, diverticular diseases, urinary incontinence, oescophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being with an effective amount of a compound of the formula (I), or a pharmaceutically acceptable salt or composition thereof.

The invention also include the novel intermediates of the formula (II).

The following Examples, in which all temperatures are in ° C., illustrate the invention.

EXAMPLE 1

Preparation of (R,S)-3-{3-(N-4-hydroxyphenethyl-N-methylamino)-3-methylbut-1-yl}-3-phenylglutarimide

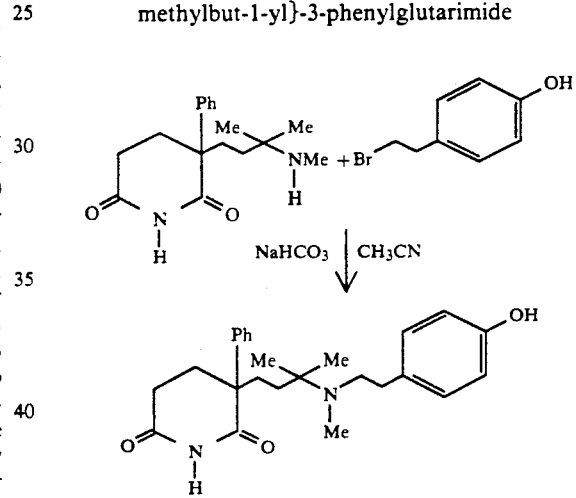

A mixture containing (R,S)-3-(3-methyl-3-methylaminobut-1-yl)-3-phenylglutarimide (0.58 g—see Preparation 11), 4-hydroxyphenethyl bromide (0.41 g), sodium bicarbonate (2 g) and acetonitrile (20 ml) was heated under reflux for 20 hours. The mixture was partitioned between dichloromethane (50 ml) and water (50 ml), the layers were separated, and the aqueous layer was further extracted with dichloromethane (2×50 ml). The combined dichloromethane extracts were dried (MgSO$_4$) and concentrated in vacuo to give a foam which was purified by column chromatography on silica eluting with dichloromethane containing methanol (0% up to 5%). The product-containing fractions were combined and concentrated in vacuo to give the title compound as a foam, yield, 0.26 g.

Analysis %:
Found: C,70.33; H,7.95; N,6.30;
Calculated for
$C_{25}H_{32}N_2O_3 \cdot \frac{1}{2}EtOH \cdot \frac{1}{2}H_2O$: C,70.87; H,8.23; N,6.36.
$^1$H-N.M.R. (CDCl$_3$)δ=8.80–7.80 (brs, 1H); 7.45–7.20 (m, 5H); 7.10–7.00 (d, 2H); 6.85–6.75 (d, 2H; 2.80–2.45 (m, 5H); 2.45–2.10 (m, 3H); 2.30 (s, 3H); 2.10–1.85 (m, 2H); 1.60–1.40 (brm, 1H); 1.35–1.20 (m, 1H); 1.00 (s, 6H) ppm.

EXAMPLE 2

Preparation of
(R,S)-3-{3-(N-4-chlorophenethyl-N-methylamino)-3-methylbut-1-yl}-3-phenylglutarimide

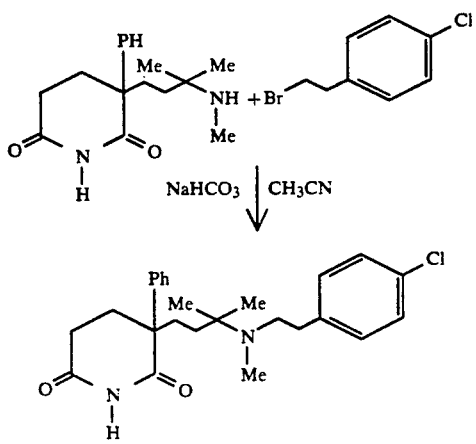

A mixture containing (R,S)-3-(3-methyl-3-methylaminobut-1-yl)-3-phenylglutarimide (0.58 g—see Preparation 11), 4-chlorophenethyl bromide (0.47 g), sodium bicarbonate (2 g) and acetonitrile (20 ml) was heated under reflux for 17 hours. The mixture was partitioned between dichloromethane (50 ml) and water (50 ml), the layers were separated, and the aqueous layer was further extracted with dichloromethane (2×50 ml). The combined dichloromethane extracts were dried (MgSO4) and concentrated in vacuo to give an oil which was purified by column chromatography on silica eluting with dichloromethane containing methanol (0% up to 4%). The product-containing fractions were combined and concentrated in vacuo to give the title compound as an oil which crystallised from ethanol, yield, 0.09 g, m.p. 135°–138° C.

Analysis %:
Found: C,70.44; H,7.53; N,6.52;
Calculated for
$C_{25}H_{31}ClN_2O_2$: C,70.32; H,7.32; N,6.56.

$^1$H-N.M.R. (CDCl$_3$)δ=7.95–7.85 (brs, 1H); 7.45–7.10 (m, 9H); 2.75–2.15 (m, 8H); 2.20 (s, 3H; 2.05–1.95 (m, 1H); 1.90–1.85 (m, 1H); 1.45–1.35 (m, 1H); 1.30–1.20 (m, 1H); 0.95 (s, 6H) ppm.

EXAMPLE 3

Preparation of
(R,S)-3-{3-(N-4-methylphenethyl-N-methylamino)-3-methylbut-1-yl}-3-phenylglutarimide

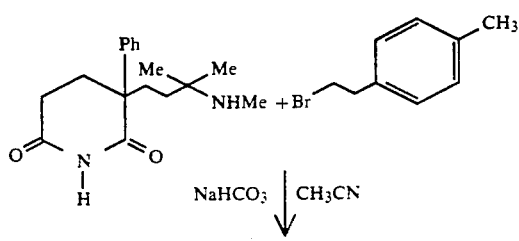

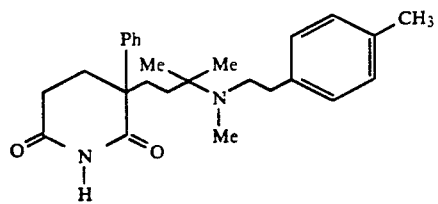

A mixture containing (R,S)-3-(3-methyl-3-methylaminobut-1-yl)-3-phenylglutarimide (0.58 g—see Preparation 11), 4-methylphenethyl bromide (0.40 g), sodium bicarbonate (2 g) and acetonitrile (20 ml) was heated under reflux for 8 hours. The mixture was partitioned between dichloromethane (50 ml) and water (50 ml), the layers were separated, and the aqueous layer further extracted with dichloromethane (2×50 ml). The combined dichloromethane extracts were dried (MgSO4) and concentrated in vacuo to give an oil which was purified by column chromatography on silica eluting with dichloromethane containing methanol (1% up to 5%). The product-containing fractions were combined and concentrated in vacuo to give the title compound as a colorless oil which was crystallised from ethanol, yield, 0.3 g. m.p. 145°–148° C.

Analysis %:
Found: C,76.81; H,8.51; N,6.83;
Calculated for
$C_{26}H_{34}N_2O_2$: C,76.81; H,8.43; N,6.89.

$^1$H-N.M.R. (CDCl$_3$)δ=7.95–7.85 (brs, 1H); 7.40–7.25 (m, 5H); 7.10 (s, 4H); 2.75–2.20 (m, 8H; 2.35 (s, 3H); 2.25 (s, 3H); 2.10–2.00 (m, 1H); 1.95–1.85 (m, 1H); 1.50–1.40 (m, 1H); 1.30–1.20 (m, 1H); 0.95 (s, 3H); 0.90 (s, 3H) ppm.

EXAMPLE 4

Preparation of
(R,S)-3-{3-(N-phenethyl-N-methylamino)-3-methylbut-1-yl}-3-phenylglutarimide

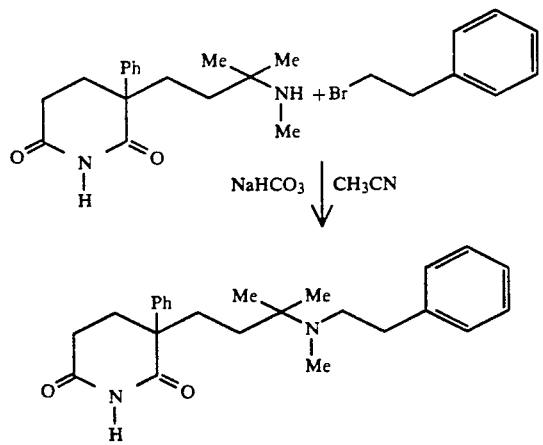

A mixture containing (R,S)-3-(3-methyl-3-methylaminobut-1-yl)-3-phenylglutarimide (0.58 g—see Preparation 11), phenethylbromide (0.38 g), sodium bicarbonate (1.0 g) and acetonitrile (20 ml) was heated under reflux for 5 hours. Water (30 ml) was added and the mixture was extracted with dichloromethane (2×50 ml). The combined dichloromethane extracts were dried (MgSO4) and concentrated in vacuo to give a gum which was purified by column chromatography on silica eluting with dichloromethane containing methanol (0% up to 10%). The product-containing fractions were combined and concentrated in vacuo to give the title compound as a colourless solid, yield, 0.14 g, m.p. 135°–137° C.

Analysis %:
Found: C,75.78; H,8.17; N,6.99;
Calculated for
$C_{25}H_{32}N_2O_2$: C,76.49; H,8.22; N,7.14.
$^1$H-N.M.R. (CDCl$_3$)δ = 8.20–8.00 (brs, 1H); 7.40–7.15 (m, 10H); 2.80–2.20 (m, 8H); 2.25 (s, 3H; 2.10–2.00 (m, 1H); 1.95–1.85 (m, 1H); 1.50–1.40 (m, 1H); 1.35–1.20 (m, 1H); 1.00 (s, 3H); 0.95 (s, 3H) ppm.

EXAMPLE 5

Preparation of
(R,S)-3-{3-(N-4-chlorophenethyl-N-methylamino)-prop-1-yl}-3-phenylglutarimide

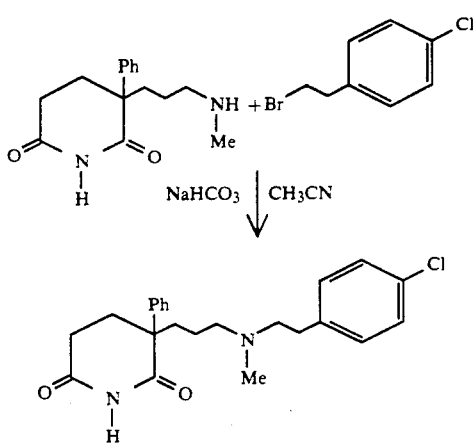

A mixture containing (R,S)-3-(3-methylaminoprop-1-yl)-3-phenylglutarimide formate (0.5 g—see Preparation 4), 4-chlorophenethyl bromide (0.42 g), sodium bicarbonate (1.0 g) and acetonitrile (20 ml) was heated under reflux for 8 hours then partitioned between dichloromethane (50 ml) and water (50 ml). the layers were separated and the aqueous layer was further extracted with dichloromethane (2×50 ml). The combined dichloromethane extracts were dried (MgSO$_4$) and concentrated in vacuo to give an oil which was purified by column chromatography on silica eluting with dichloromethane containing methanol (0% up to 8%). The product-containing fractions were combined and concentrated in vacuo to give a foam which was further purified by column chromatography on silica eluting with chloroform containing methanol (0% up to 8%). The product containing factions were combined and concentrated in vacuo to give the title compound as a colourless foam, yield, 0.06 g.

Analysis %:
Found: C,68.17; H,6.76; N,6.74;
Calculated for
$C_{23}H_{27}ClN_2O_2 \cdot \frac{1}{2}H_2O$: C,67.71; H,6.92; N,5.87.
$^1$H-N.M.R. (CDCl$_3$)δ = 8.00–7.95 (brs, 1H); 7.40–7.25 (m, 7H); 7.15–7.10 (d, 2H); 2.75–2.20 (m, 10H); 2.25 (s, 3H); 2.05–1.80 (m, 2H); 1.60–1.30 (m, 2H) ppm.

EXAMPLE 6

Preparation of
(R,S)-3-{3-(N-4-methylphenethyl-N-methylamino)-prop-1-yl}-3-phenylglutarimide

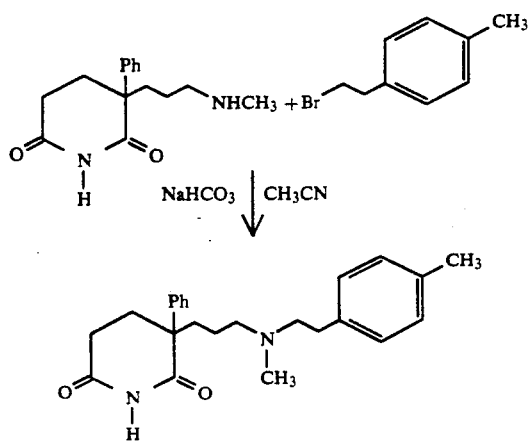

A mixture containing (R,S)-3-(3-methylaminoprop-1-yl)-3-phenylglutarimide (0.5 g—see Preparation 4), 4-methylphenethyl bromide (0.38 g), sodium bicarbonate (1.0 g) and acetonitrile (20 ml) was heated under reflux for 8 hours then partitioned between dichloromethane (50 ml) and water (50 ml). The layers were separated, and the aqueous layer was further extracted with dichloromethane (3×50 ml). The combined dichloromethane extracts were dried (MgSO$_4$) and concentrated in vacuo to give a foam which was purified by column chromatography on silica eluting with dichloromethane containing methanol (0% up to 6%). The product-containing fractions were combined and concentrated in vacuo to give a foam which was further purified by column chromatography on silica eluting with chloroform containing methanol (0% to 8%). The product-containing fractions were combined and concentrated in vacuo to give the title compound as a colourless foam, yield, 0.09 g.

Analysis %:
Found: C,70.55; H,7.47; N,6.81;
Calculated for
$C_{24}H_{30}N_2O_2 \cdot H_2O \cdot \frac{1}{4}CHCl_3$: C,70.96; H,7.92; N,6.83.
$^1$H-N.M.R. (CDCl$_3$)δ = 7.95–7.85 (brs, 1H); 7.45–7.25 (m, 5H); 7.15–7.05 (Abq, 4H); 2.75–2.50 (m, 5H; 2.50–2.20 (m, 4H); 2.35 (s, 3H); 2.25 (s, 3H); 2.10–1.85 (m, 2H); 1.75–1.35 (m, 3H) ppm.

EXAMPLE 7

Preparation of
(R,S)-3-[3[N-{2-(indan-5-yl)ethyl}-N-methylamino]-prop-1-yl]-3-phenylglutarimide

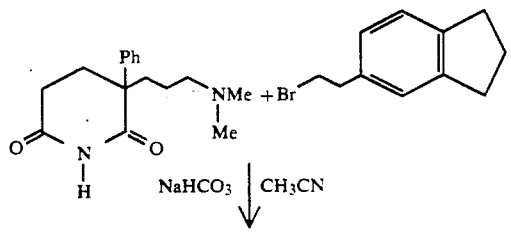

-continued

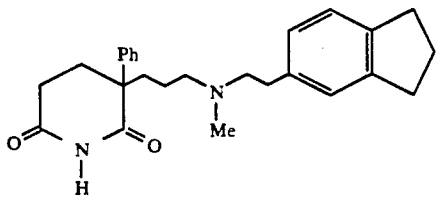

A mixture containing (R,S)-3-(3-methylaminoprop-1-yl)-3-phenylglutarimide (0.5 g—see Preparation 4), 5-(2-bromoethyl)indane (0.43 g—see Preparation 12), sodium bicarbonate (1.0 g) and acetonitrile (20 ml) was heated under reflux for 8 hours then partitioned between dichloromethane (50 ml) and water (50 ml). the layers were separated, and the aqueous layer was further extracted with dichloromethane (3×50 ml). The combined dichloromethane extracts were dried (MgSO$_4$) and concentrated in vacuo to give a foam which was purified by column chromatography on silica eluting with dichloromethane containing methanol (0% up to 8%). The product-containing fractions were combined and concentrated in vacuo to give a foam which was further purified by column chromatography on silica eluting with chloroform containing methanol (0% to 5%). The product-containing fractions were combined and concentrated in vacuo to give the title compound as a colourless foam, yield, 0.09 g.

Analysis %:
Found: C,75.07; H,7.82; N,6.87;
Calculated for
C$_{26}$H$_{32}$N$_2$O$_2$·½H$_2$O: C,75.51; H,7.80; N,6.77.

$^1$H-N.M.R. (CDCl$_3$)δ=8.05-7.95 (brs, 1H); 7.45-7.20 (m, 5H); 7.20-7.15 (d, 1H); 7.05 (s, 1H); 6.95-6.90 (d, 1H); 2.95-2.85 (t, 4H); 2.75-2.70 (m, 2H); 2.6514 2.50 (m, 2H); 2.50-2.30 (m, 4H); 2.30-2.20 (m, 2H); 2.30 (s, 3H); 2.15-1.85 (m, 4H); 1.60-1.35 (m, 2H) ppm.

EXAMPLE 8

Preparation of
(R,S)-3-{3-(N-phenethyl-N-methylamino)-prop-1-yl]-3-phenylglutarimide

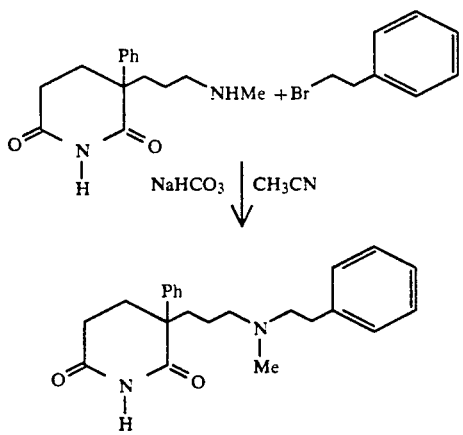

A mixture containing (R,S)-3-(3-methylaminoprop-1-yl)-3-phenylglutarimide (0.5 g—see Preparation 4), phenethyl bromide (0.35 g), sodium bicarbonate (1.0 g) and acetonitrile (20 ml) was heated under reflux for 8 hours then partitioned between dichloromethane (50 ml) and water (30 ml). The layers were separated, and the aqueous layer was further extracted with dichloromethane (3×30 ml). The combined dichloromethane extracts were dried (MgSO$_4$) and concentrated in vacuo to give a gum which was purified by column chromatography on silica eluting with dichloromethane containing methanol (0% up to 8%). The product-containing fractions were combined and concentrated in vacuo to give the title compound as a foam, yield, 0.09 g.

Analysis %:
Found: C,73.95; H,7.65; N,7.59;
Calculated for
C$_{23}$H$_{28}$N$_2$O$_2$·½H$_2$O: C,73.96; H,7.55; N,7.50.

$^1$H-N.M.R. (CDCl$_3$)δ=8.05-7.95 (brs, 1H); 7.45-7.10 (m, 10H); 2.80-2.70 (m, 2H); 2.70-2.50 (m, 3H); 2.50-2.30 (m, 4H); 2.30-2.20 (m, 1H); 2.25 (s, 3H); 2.10-1.85 (m, 2H); 1.60-1.30 (m, 2H) ppm.

EXAMPLE 9

Preparation of
(R,S)-3-{3-(N-benzyl-N-methylamino)-prop-1-yl]-3-phenylglutarimide

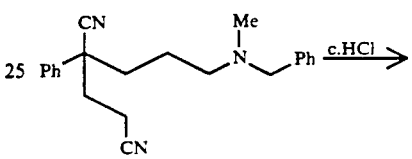

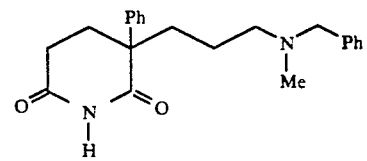

A solution of (R,S)-6-(N-benzyl-N-methylamino)-1,3-dicyano-3-phenylhexane (19.0 g—see Preparation 3) in concentrated hydrochloric acid (100 ml) was heated under reflux for 2 hours. Water (500 ml) was added cautiously and the mixture neutralized (pH 8) by the addition of sodium bicarbonate. The mixture was extracted with dichloromethane (3×150 ml), the extracts were combined then dried (MgSO$_4$) and concentrated in vacuo to give the title compound as a gum, yield, 15.0 g.

$^1$H-N.M.R. (CDCl$_3$)δ=8.30-8.20 (brs, 1H); 7.45-7.20 (m, 10H); 3.45 (s, 2H); 2.65-2.55 (m, 1H); 2.50-2.25 (m, 4H); 2.15 (s, 3H); 2.10-1.85 (m, 3H); 1.65-1.40 (m, 2H) ppm.

EXAMPLE 10

Preparation of
(R,S)-3-{3-(N-benzyl-N-methylamino)-3-methylbut-1-yl]-3-phenylglutarimide

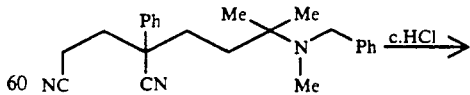

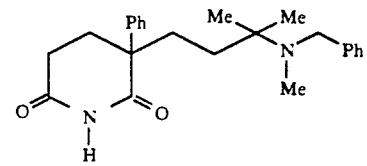

A solution of (R,S)-6-(N-benzyl-N-methylamino)-1,3-dicyano-6-methyl-3-phenylheptane (14.0 g—see Preparation 10) in concentrated hydrochloric acid (70 ml) was heated under reflux for 2 hours. The mixture was diluted with water (100 ml) and basified (pH 8) by the addition of sodium bicarbonate. The mixture was extracted with dichloromethane (3×150 ml) and the combined extracts dried (MgSO₄) and concentrated in vacuo to give the title compound as a brown oil which crystallised on standing, yield, 11 g. A sample recrystallised from ethanol had m.p. 104°-106° C.

Analysis %:
Found: C,76.48; H,7.90; N,7.24;
Calculated for
$C_{24}H_{30}N_2O_2$: C,76.15; H,7.99; N,7.40.

¹H-N.M.R. (CDCl₃)δ=7.90-7.80 (brs, 1H); 7.40-7.20 (m, 10H); 3.45 (s, 2H); 2.65-2.05 (m, 5H); 2.00 (s, 3H); 1.65-1.50 (m, 2H); 1.45-1.30 (m, 1H); 1.05 (s, 6H) ppm.

The following Preparations illustrate the preparation of the novel starting materials in the previous Examples:

Preparation 1

Preparation of
3-(N-benzyl-N-methylamino)-1-chloropropane hydrochloride

[See also J. Chem. Soc., (1944), 269.]

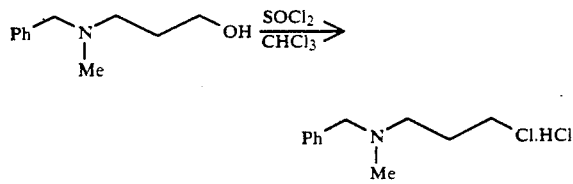

Thionyl chloride (22 ml) was added dropwise to a cooled (0° C.) solution of 3-(N-benzyl-N-methylamino)-propan-1-ol (32.8 g) in chloroform (100 ml). The mixture was allowed to warm to room temperature and then heated under reflux for 1 hour. The mixture was concentrated in vacuo to give an oil which was triturated with ethyl acetate to give the title compound as a colourless powder, yield, 32 g.

¹H-N.M.R. (CDCl₃)δ=7.70-7.60 (m, 2H); 7.50-7.40 (m, 3H); 4.35-4.15 (m, 2H); 3.75-3.60 (m, 2H); 3.35-3.25 (m, 1H); 3.15-3.00 (m, 1H); 2.75 (d, 3H); 2.60-2.50 (m, 1H); 2.45-2.30 (m, 1H) ppm.

Preparation 2

Preparation of
(R,S)-4-(N-benzyl-N-methylamino)-1-cyano-1-phenylbutane

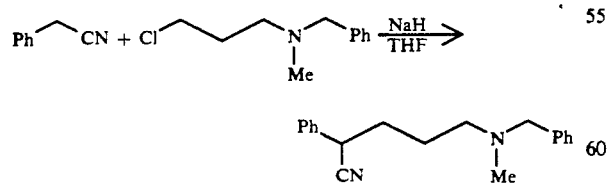

Sodium hydride (4.5 g of a 60% dispersion in mineral oil) was added in portions to a solution of phenylacetonitrile (11.7 g) in anhydrous tetrahydrofuran (100 ml). When the addition was complete, the mixture was heated under reflux for 20 minutes then allowed to cool to room temperature. 3-(N-benzyl-N-methylamino)-1-chloropropane hydrochloride (15.0 g—see Preparation 1) was ground up with sodium hydroxide pellets to give an oil which was dissolved in anhydrous tetrahydrofuran (100 ml) and added dropwise to the phenylacetonitrile solution. The mixture was heated under reflux for 1.5 hours. The tetrahydrofuran was evaporated in vacuo and the reside partitioned between dichloromethane (200 ml) and water (100 ml). The mixture was adjusted to pH7 by the addition of solid carbon dioxide, the layers were separated, and the aqueous layer was further extracted with dichloromethane (2×100 ml). The combined dichloromethane extracts were dried (MgSO₄) and concentrated in vacuo to give an oil which was purified by column chromatography on silica eluting with dichloromethane containing methanol (0% up to 8%). The product-containing fractions were combined and concentrated in vacuo to give the title compound as an oil, yield, 15.4 g.

¹H-N.M.R. (CDCl₃)δ=7.50-7.25 (m, 10H); 3.85-3.75 (t, 1H); 3.50 (s, 2H); 2.50-2.40 (t, 2H); 2.20 (s, 3H); 2.05-1.90 (m, 2H); 1.75-1.65 (m, 2H) ppm.

Preparation 3

Preparation of
(R,S)-6-(N-benzyl-N-methylamino)-1,3-di-cyano-3-phenylhexane

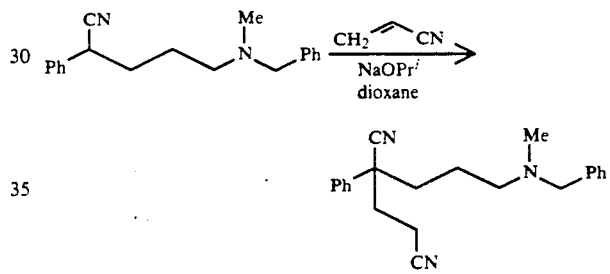

Sodium hydride (0.2 g of a 60% dispersion in mineral oil) was added to propan-2-ol (2 ml) and the resulting solution was added to a solution of 4-(N-benzyl-N-methylamino)-1-cyano-1-phenylbutane (15.0 g—see Preparation 2) and acrylonitrile (4.0 ml) in 1,4-dioxane (100 ml). The mixture was stirred at room temperature for 20 hours then concentrated in vacuo. Water (100 ml) was added and the mixture was neutralized (pH 7) by the addition of solid carbon dioxide then extracted with dichloromethane (3×50 ml). The combined dichloromethane extracts were dried (MgSO₄) and concentrated in vacuo to give the title compound as a gum, yield, 19 g.

¹H-N.M.R. (CDCl₃)δ=7.50-7.25 (m, 10H); 3.45 (s, 2H); 2.65-2.20 (m, 5H); 2.20-2.00 (m, 3H); 2.10 (s, 3H); 1.75-1.60 (m, 1H); 1.40-1.25 (m, 1H) ppm.

Preparation 4

Preparation of
(R,S)-3-(3methylaminoprop-1-yl)-3-phenylglutarimide formate

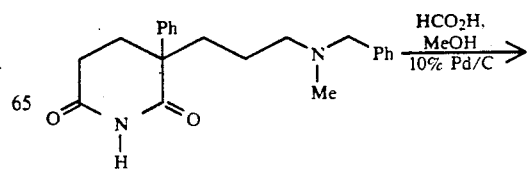

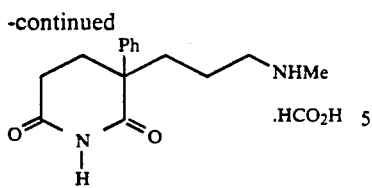

10% Palladium-on-carbon (5 g) was added in portions to a cooled (0° C.) solution of (R,S)-3-{3-(N-benzyl-N-methylamino)-prop-1-yl}3-phenylglutarimide (15.0 g—see Preparation 9) in methanol (100 ml) and formic acid (15 ml. The mixture was allowed to warm to room temperature and stirred for 16 hours then filtered and concentrated in vacuo to give the title compound as a gum, yield, 15 g.

¹H-N.M.R. (CDCl₃)δ=9.60-9.20 (brs, 1H); 8.35-8.20 (s, 2H); 7.40-7.15 (m, 5H); 3.00-2.85 (m, 2H); 2.65 (s, 3H); 2.65-2.45 (1H); 2.40-2.20 (m, 3H); 2.10-1.75 (m, 3H); 1.70-1.50 (brs, 1H ppm.

Preparation 5

Preparation of ethyl 3-methyl-3-methylaminobutanoate

[See also J. Chem. Soc., 33, 1322, (1968)]

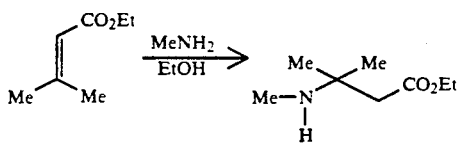

A mixture containing ethyl 3,3-dimethylacrylate (100 g) and methylamine (140 ml of a 33% solution in ethanol) in ethanol (400 ml) was allowed to stand at room temperature for 2 weeks. The mixture was concentrated in vacuo to give an oil which was fractionally distilled in vacuo to give the title compound as a colourless, mobile oil, yield, 95.0 g, b.p. 68°-75°/20 mm.Hg.

¹H-N.M.R. (CDCl₃)δ=4.1 (q, 2H); 2.40 (s, 2H); 2.30 (s, 3H); 1.60 (brs, 1H); 1.25 (t, 3H); 1.15 (s, 6H) ppm.

Preparation 6

Preparation of ethyl 3-(N-benzyl-N-methylamino)-3-methylbutanoate

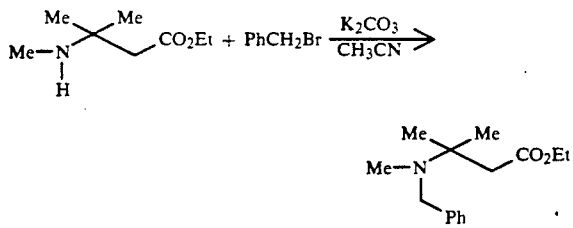

A mixture containing ethyl 3-methyl-3-methylaminobutanoate (95 g—Preparation 5), benzyl bromide (72 ml), anhydrous potassium carbonate (138 g) and acetonitrile (500 ml) was heated under reflux for 1.5 hours. The mixture was concentrated in vacuo and the residue partitioned between dichloromethane (500 ml) and 10% aqueous potassium carbonate (300 ml). The layers were separated and the aqueous layer extracted with dichloromethane (2 ×100 ml). The combined dichloromethane extracts were dried (MgSO₄) and concentrated in vacuo to give an the title compound as a mobile, colourless oil, yield, 150 g.

¹H-N.M.R. (CDCl₃)δ=7.40-7.20 (m, 5H); 4.20 (q, 2H); 3.60 (s, 2H); 2.55 (s, 2H); 2.15 (s, 3H); 1.35 (s, 6H); 1.30 (t, 3H) ppm.

Preparation 7

Preparation of 3-(N-benzyl-N-methylamino)-3-methylbutan-1-ol

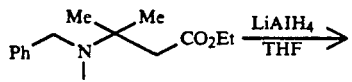

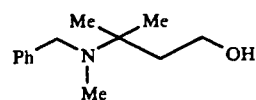

A solution of ethyl 3-(N-benzyl-N-methylamino)-3-methylbutanoate (23.6 g—Preparation 6), in anhydrous tetrahydrofuran (100 ml) was added, dropwise, over 20 minutes to a stirred suspension of lithium aluminum hydride (7.2 g) in anhydrous tetrahydrofuran (300 ml). When the addition was complete, the mixture was stirred at room temperature for 3 hours. Water (7 ml) was carefully added dropwise followed by 15% aqueous sodium hydroxide (7 ml) and finally more water (20 ml). The resulting solid precipitate was filtered off and washed with ethyl acetate (3 ×50 ml). The filtrate and washings were combined and concentrated in vacuo to give the title compound as a colourless, mobile oil, yield, 19.0 g.

¹H-N.M.R. (CDCl₃)δ=7.40-7.20 (m, 5H); 6.15 (brs, 1H); 3.95 (t, 2H); 3.65 (s, 2H); 2.15 (s, 3H); 1.80 (t, 2H); 1.25 (s, 6H) ppm.

Preparation 8

Preparation of 2-(N-benzyl-N-methylamino)-4-chloro-2-methylbutane hydrochloride

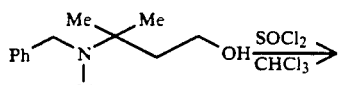

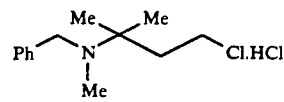

A solution of 3-(N-benzyl-N-methylamino)-3-methylbutan-1-ol (6.9 g—Preparation 7), in chloroform (20 ml) was added dropwise over 30 minutes to a solution of thionyl chloride (4.9 ml) in chloroform (20 ml) at 0°. When the addition was complete, the mixture was stirred at room temperature for 18 hours. Ethanol (5 ml) was added and the mixture concentrated in vacuo to give an oil which was crystallized from ethyl acetate to give the title compound as a colourless powder, yield, 2.62 g, m.p. 164°-166°.

¹H-N.M.R. (CDCl₃)δ=7.75 (m, 2H); 7.50-7.40 (m, 3H); 4.70 (dd, 1H); 3.80-3.65 (m, 3H); 2.60-2.45 (m, 5H); 1.70 (d, 6H) ppm.

Preparation 9

Preparation of (R,S)-4-(N-benzyl-N-methylamino)-1-cyano-4-methyl-1-phenylpentane

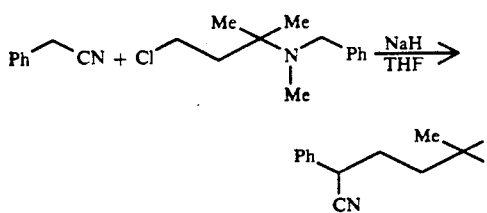

Sodium hydride (4.4 g of a 60% dispersion in mineral oil) was added in portions to a solution of phenylacetonitrile (11.7 g) in anhydrous tetrahydrofuran and the mixture was heated under reflux for 15 minutes. The resulting yellow suspension was cooled to room temperature whereupon 2-(N-benzyl-N-methylamino)-4-chloro-2-methylbutane (20 g—freshly prepared from its hydrochloride salt by partitioning between dichloromethane and 15% aqueous sodium hydroxide—see Preparation 8) was added and the mixture heated under reflux for 0.5 hour. The tetrahydrofuran was evaporated in vacuo and the residue partitioned between dichloromethane (200 ml) and water (100 ml). The layers were separated and the aqueous layer was neutralized (pH 7) by the addition of solid carbon dioxide. The aqueous solution was extracted with dichloromethane (2×100 ml), the dichloromethane extracts were combined then dried (MgSO$_4$) and concentrated in vacuo to give a waxy solid which was purified by column chromatography on silica eluting with toluene containing diethyl ether (10% up to 40%. The product-containing fractions were combined and concentrated in vacuo to give the title compound as an orange oil, yield, 17.1 g.

$^1$H-N.M.R. (CDCl$_3$)δ=7.50–7.20 (m, 10H); 3.85–3.75 (m, 2H); 3.50 (s, 1H); 2.20–2.05 (m, 2H); 2.05 (s, 3H); 1.75–1.60 (m, 2H); 1.10 (s, 6H) ppm.

Preparation 10

Preparation of (R,S)-6-(N-benzyl-N-methylamino)-1,3-di-cyano-6-methyl-3-phenylheptane

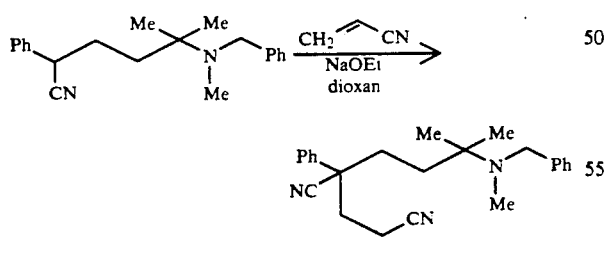

Sodium (0.46 g) was dissolved in ethanol (10 ml) and the resulting solution was added dropwise to a solution of (R,S)-4-(N-benzyl-N-methylamino)-1-cyano-4-methyl-1-phenylpentane (17.5 g—see Preparation 9) and acrylonitrile (3.18 ml) in 1,4-dioxane (30 ml). The mixture was warmed to 55° C. then allowed to cool. A further quantity of acrylonitrile (4 ml) was added and the mixture was stirred at room temperature for 2 hours. The mixture was partitioned between dichloromethane (150 ml) and water (100 ml) then neutralized (pH 7) by the addition of solid carbon dioxide. The layer were separated and the aqueous layer was further extracted with dichloromethane (2×100 ml). The combined dichloromethane extracts were dried (MgSO$_4$) and concentrated in vacuo to give an oil which was partially purified by column chromatography on silica eluting with dichloromethane containing methanol (0% up to 10%). The product-containing fractions were combined and concentrated in vacuo to give an oil which was further purified by column chromatography on silica eluting with toluene containing ethyl acetate (15%). The product-containing fractions were combined and concentrated in vacuo to give the title compound as a gum, yield, 14 g.

$^1$H-N.M.R. (CDCl$_3$)δ=7.45–7.15 (m, 10H); 3.50–3.35 (Abq, 2H); 2.60–2.05 (m, 4H); 2.00 (s, 3H); 1.70–1.60 (m, 2H); 1.30–1.20 (m, 2H); 1.10 (s, 3H); 1.00 (s, 3H) ppm.

PREPARATION 11

Preparation of (R,S)-3-(3-methyl-3-methylaminobut-1-yl)-3-phenylglutarimide

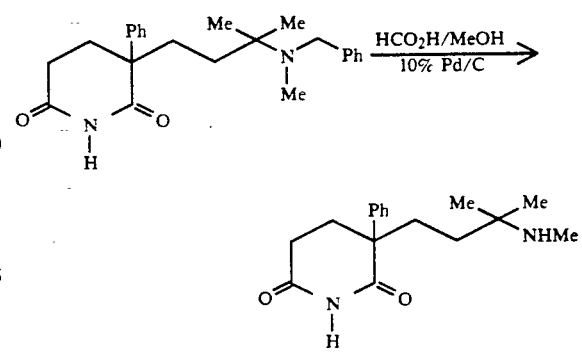

10% Palladium-on-carbon (5 g) was added in portions to a cooled (0° C.) solution of (R,S)-3-{3-(N-benzyl-N-methylamino)-3-methylbut-1-yl}-3-phenylglutarimide (10.5 g—see Example 10) in methanol (100 ml) containing formic acid (11 ml). The mixture was allowed to warm to room temperature and stirred for 16 hours then filtered and concentrated in vacuo to give the title compound as a gum, yield, 7.1 g.

$^1$H-N.M.R. (CDCl$_3$)δ=7.45–7.25 (m, 5H); 2.65–2.55 (m, 1H); 2.50–2.20 (m, 3H); 2.30 (s, 3H); 2.10–1.95 (m, 1H); 1.95–1.85 (m, 1H); 1.55–1.45 (m, 1H); 1.35–1.25 (m, 1H); 1.10 (s, 3H); 1.05 (s, 3H) ppm.

PREPARATION 12

Preparation of 5-(2-bromoethyl)indane

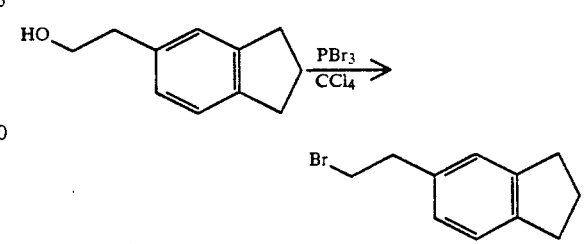

Phosphorus tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate. The layers were separated and the aqueous layer extracted with dichloromethane (2 ×100 ml). The combined dichloromethane extracts were dried (MgSO$_4$) and concentrated in vacuo to give an oil which was purified by column chromatography on silica eluting with dichloromethane. The product-containing fractions were combined and concentrated in vacuo to give the title compound as a colourless oil, yield 10.5 g.

$^1$H-N.M.R. (CDCl$_3$)δ=7.30-7.00 (m, 3H); 3.60 (m, 2H); 3.20 (m, 2H); 3.00-2.85 (m, 4H); 2.20-2.05 (m, 2H) ppm.

We claim:

1. A compound of the formula:

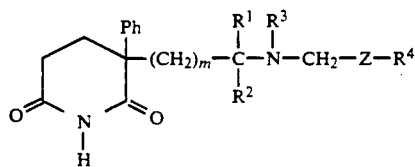

or a pharmaceutically acceptable salts thereof, where
m is 1 or 2;
R$^1$ and R$^2$ are each independently H or C$_1$-C$_4$ alkyl or together represent —(CH$_2$)$_p$— where p is an integer of from 2 to 5;
R$^3$ is H or C$_1$-C$_4$ alkyl;
wherein
Z is a direct link; —CH$_2$—, —CH$_2$O— or —CH$_2$S—; and
R$^4$ is a group of the formula:

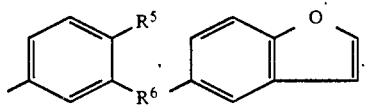

-continued

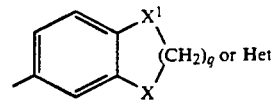

where
R$^5$ and R$^6$ are each independently H, C$_1$-C$_4$ alkyl, C$_1$-C$_4$ alkoxy, —(CH$_2$)$_n$OH, halo, trifluoromethyl, cyano, —(CH$_2$)$_n$NR$^7$R$^8$, —CO(C$_1$-C$_4$ alkyl), —O-CO(C$_1$-C$_4$ alkyl), —CH(OH)(C$_1$-C$_4$ alkyl), —C(OH)(C$_1$-C$_4$ alkyl)$_2$, —SO$_2$NH$_2$, —(CH$_2$)$_n$CONR$^7$R$^8$ or —(CH$_2$)$_n$COO(C$_1$-C$_4$ alkyl);
R$^7$ and R$^8$ are each independently H or C$_1$-C$_4$ alkyl;
n is 0, 1 or 2;
X and X$^1$ are each independently O or CH$_2$;
q is 1, 2 or 3; and
"Het" is pyridyl, pyrazinyl or thienyl.

2. A compound as claimed in claim 1 wherein m is 2.

3. A compound as claimed in claim 2 wherein in which R$^1$ and R$^2$ are each H or CH$_3$.

4. A compound as claimed in claim 3 wherein R$^3$ is methyl and Z is —CH$_2$—.

5. A compound as claimed in claim 4 wherein R$^4$ is a group of the formula:

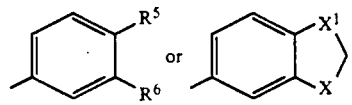

where R$^5$ and R$^6$ are each independently selected from H, halo, hydroxy and C$_1$-C$_4$ alkyl, and X and X$^1$ are each independently O or CH$_2$.

6. A pharmaceutical composition comprising a compound of the formula (I) as claimed in claim 1, or a pharmaceutically acceptable salt thereof, and a pharmaceutically acceptable diluent or carrier.

7. A compound as claimed in claim 5 wherein R$^5$ and R$^6$ are each independently H.

8. A method of treating irritable bowel syndrome in a patient, which comprises administering to said patient an effective amount of a compound or pharmaceutically acceptable salt thereof as claimed in claim 1.

* * * * *